United States Patent [19]

Dekeyser et al.

[11] Patent Number: 4,670,555
[45] Date of Patent: Jun. 2, 1987

[54] SUBSTITUTED OXADIAZINONES

[75] Inventors: Mark A. Dekeyser, Waterloo; Anupama Mishra, Wellington, both of Canada; Richard C. Moore, New Haven, Conn.

[73] Assignees: Uniroyal Chemical Company, Inc., Middlebury, Conn.; Uniroyal Ltd., Don Mills, Canada

[21] Appl. No.: 725,029

[22] Filed: Apr. 19, 1985

[51] Int. Cl.$^4$ ............................................. C07D 273/04
[52] U.S. Cl. .................................................. 544/68
[58] Field of Search ........................................ 544/68

[56] References Cited

PUBLICATIONS

Van Alphen, Recueil, vol. 43 (1924), pp. 841–844.
Van Alphen, Recueil, vol. 47 (1928), pp. 909–919.
Van Alphen, Recueil, vol. 48 (1929), pp. 163–172 & 417–421.
Hoppenbrouwers, Recueil, vol. 53 (1934), pp. 325–354.

*Primary Examiner*—Richard L. Raymond
*Attorney, Agent, or Firm*—Wiliam E. Dickheiser

[57] ABSTRACT

A compound having the structural formula

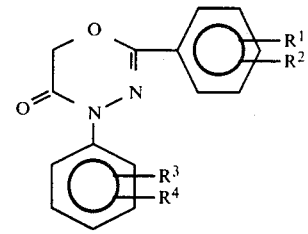

where $R^1$ and $R^2$ are the same or different and are hydrogen; however, both $R^1$ and $R^2$ cannot be hydrogen if $R^3$ and $R^4$ are both hydrogen or if one of $R^3$ and $R^4$ is hydrogen and the other nitro; in addition $R^1$ and $R^2$ may be the same or different and may be fluorine, chlorine, bromine, iodine, $C_1$–$C_6$ alkyl, $C_1$–$C_2$ haloalkyl, $C_3$–$C_6$ cycloalkyl, $C_7$–$C_9$ aralkyl, phenyl, $C_1$–$C_6$ alkoxy, $C_1$–$C_6$ alkylthio, $C_1$–$C_6$ alkylsulfinyl, $C_7$–$C_9$ aralkoxy, phenoxy, provided that if both $R^3$ and $R^4$ are hydrogen, then $R^1$ and $R^2$ cannot be 3-phenoxy and hydrogen; also $R^1$ and $R^2$ may be the same or different and may be phenylthio, phenylsulfonyl, alkali metal carboxylate, $C_2$–$C_5$ alkoxycarbonyl, phenoxycarbonyl or —$NR^5R^6$; $R^3$ and $R^4$ are the same or different and are $C_1$–$C_4$ alkylsulfonyl, nitro; provided that if the other of $R^3$ and $R^4$ is hydrogen then $R^1$ and $R^2$ cannot both be hydrogen, also $R^3$ and $R^4$ may be the same or different and may be —$OCX_nH_{3-n}$ or any of the meanings given for $R^1$ and $R^2$ with the proviso that if $R^3$ and $R^4$ are together hydrogen and bromine then if $R^1$ and $R^2$ are both hydrogen the bromine cannot be 4-bromo; $R^5$ and $R^6$ are the same or different and are hydrogen or $C_1$–$C_2$ alkyl with the proviso that when $R^5$ and $R^6$ are both hydrogen then $R^1$, $R^2$ and $R^3$ cannot all be hydrogen; X is fluorine, chlorine or bromine; and n is 1, 2 or 3 is disclosed. The compounds of this invention are effective as a nematocidal and/or a miticidal agent. A process for forming these compounds is also set forth.

3 Claims, No Drawings

SUBSTITUTED OXADIAZINONES

BACKGROUND OF THE INVENTION

1. Field of the Invention

The instant invention is directed to a class of oxadiazinones. More specifically, the instant invention is directed to a class of oxadiazinones useful as miticides and nematocides.

2. Background of the Prior Art

The devastation caused by mites and nematodes represent a serious economic threat to commercially important food, fiber and ornamental plants. For this reason the development of new, more effective miticides and nematocides represents an ongoing scientific activity. Oxadiazinones, distinguished from the compounds of the present invention, are known in the art. However, there is no disclosure suggesting the use of oxadiazinones as a pesticide, let alone as a nematocide or a miticide. Indeed, most disclosures of substituted and unsubstituted oxadiazinones set forth no use or suggest utility in only the most general terms.

Van Alphen, *Recueil*, Vol. 47, pp 909-919 (1928); *Recueil*, Vol. 48, pp 163-172 (1929); and *Recueil*, Vol. 48, pp 417-421 (1929) all disclose substituted 1,3,4-oxadiazin-5-ones. These early papers disclose among other non-relevant compounds, only phenyl substitution at the 2 and/or 4 positions. Significantly, none of the three papers disclose any utility for the compounds discussed therein.

Hoppenbrouwers, *Recueil*, Vol. 53, pp 325-354 (1934) sets forth substituted 1,3,4-oxadiazin-5-ones including phenyl, nitrophenyl and bromophenyl substitutions at the 2- and 4-positions. Again, no utility is disclosed or demonstrated for the compounds recited therein.

Gaozza et al., *J. Heterocyclic Chem.*, pp 927-930, (1970) also has as its subject substituted 1,3,4-oxadiazin-5-ones. Among the compounds mentioned is a 2-hydroxyphenyl, 4-phenyl substituted 1,3,4-oxadiazin-5-one. Like the earlier discussed references, no utility is set forth for the compounds mentioned.

Sicardi et al., *J. Pharm. Sci.*, Vol. 63, pp. 1336-1337 (1974) is concerned with 1,3,4-oxidiazin-5-ones. Among those of interest are those having a 2-hydroxyphenyl substituent in the 2-position. However, compounds having this substitution have an alkyl, benzyl, morpholinoalkyl or phenoxyethyl substituent in the 4-position. The only mention of utility is a speculation that these compounds have "potential" psychopharmacological use. No such utility is exemplified.

Westphal et al., *J. Prakt. Chem.*, Vol, 320, pp. 452-456 (1978) teaches 2,4-diphenyl-1,3,4-oxadiazin-5-ones carrying hydrazine, benzylamino, phthalimido or succinimido moieties in the 6-position. No utility for the disclosed compounds is recited.

Rosenblum et al., *J. Am. Chem. Soc.*, Vol 85, pp. 3874-3878 (1963) discloses substituted 1,3,4-oxadiazin-2-ones. The disclosed compounds are structurally distinguished from the 1,3,4-oxadiazin-5-ones of the remaining references and the useful compounds of the present invention.

Takamizawa et al., *Chem Pharm. Bull.*, Vol. 23, pp. 948-954 (1975) discloses 1,3,4-oxadiazin-5-one derivatives having a substituted phenyl group in the 2-position, ethyl in the 4-position and unsubstituted or substituted phenyl in the 6-position. The reference is devoid of any utility for these disclosed compounds.

European Patent Application 80,296, published Jan. 6, 1983 is directed to pharmaceutically active phenyl-, thia-, oxa- or triazinones. Among the compounds disclosed in this application are 1,3,4-oxadiazin-5-ones having, as the only substituent, substituted phenyl in the 2-position. These compounds are recited to be useful as cardiotonic agents.

All of the references mentioned above, relating to compounds similar to those of the present invention, advance the art. However, none of them disclose a particular class of compounds providing excellent miticidal and/or nematocidal activity.

SUMMARY OF THE INVENTION

The instant invention is directed to a class of substituted oxadiazinones which provide excellent nematocidal and miticidal activity.

In accordance with the instant invention a class of substituted oxadiazinones having the structural formula

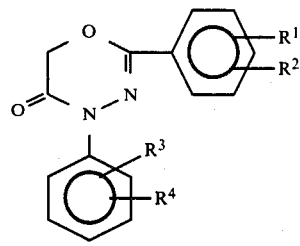

where $R^1$ and $R^2$ are the same or different and are hydrogen; however $R^1$ and $R^2$ both cannot be hydrogen if $R^3$ and $R^4$ both are hydrogen or if one of $R^3$ and $R^4$ is hydrogen and the other nitro; in addition $R^1$ and $R^2$ may be the same or different and may be fluorine, chlorine, bromine, iodine, $C_1$-$C_6$ alkyl, $C_1$-$C_2$ haloalkyl, $C_3$-$C_6$ cycloalkyl, $C_7$-$C_9$ aralkyl, phenyl, $C_1$-$C_6$ alkoxy, $C_1$-$C_6$ alkylthio, $C_1$-$C_6$ alkylsulfinyl, $C_7$-$C_9$ aralkoxy, phenoxy; provided that if both $R^3$ and $R^4$ are hydrogen then $R^1$ and $R^2$ cannot be 3-phenoxy and hydrogen; also $R^1$ and $R^2$ may be the same or different and may be phenylthio, phenylsulfonyl, alkali metal carboxylate, $C_2$-$C_5$ alkoxycarbonyl, phenoxycarbonyl or $-NR^5R^6$;

$R^3$ and $R^4$ are the same or different and are $C_1$-$C_4$ alkylsulfonyl, nitro; provided that if the other of $R^3$ and $R^4$ is hydrogen then both $R^1$ and $R^2$ cannot be hydrogen; also $R^3$ and $R^4$ may be the same or different and may be $-OCX_nH_{3-n}$ or one of the meanings of $R^1$ and $R^2$ with the proviso that if $R^3$ and $R^4$ are together hydrogen and bromine when $R^1$ and $R^2$ are both hydrogen then the bromine cannot be 4-bromo;

$R^5$ and $R^6$ are the same or different and are hydrogen or $C_1$-$C_2$ alkyl with the proviso that when $R^5$ and $R^6$ are both hydrogen then $R^1$, $R^2$ and $R^3$ cannot all be hydrogen;

X is fluorine, chlorine or bromine; and n is 1, 2 or 3 is disclosed having utility as a miticide or a nematodicide.

In further accordance with the instant invention a process for making substituted oxadiazinones is provided. In this process a compound of the formula $R^1R^2C_6H_3COCl$ is reacted with a compound of the formula $R^3R^4C_6H_3NHNH_2$ to produce a first intermediate compound of the formula $R^1R^2C_6H_3CONHNHC_6H_3R^3R^4$ where $R^1$, $R^2$, $R^3$ and $R^4$ have the meanings given above defining the compounds of this invention. The thus formed first intermediate compound is reacted with chloroacetyl chloride to produce a second intermediate compound, $R^1R^2C_6H_3CONHN(COCH_2Cl)C_6H_3R^3R^4$. This second intermediate compound is cyclizied with the addition of potassium carbonate to produce the substituted oxadiazinones of the present invention.

In still further accordance with the instant invention a process is provided for controlling mites. In this process a miticidally effective amount of a compound of the formula

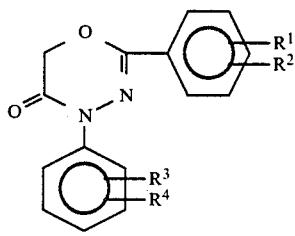

where $R^1$ and $R^2$ are the same or different and are hydrogen, fluorine, chlorine, bromine, iodine, $C_1$-$C_2$ fluoroalkyl, $C_1$-$C_2$ chloroalkyl, $C_1$-$C_2$ bromoalkyl, $C_1$-$C_6$ alkyl, $C_3$-$C_6$ cycloalkyl, $C_7$-$C_9$ aralkyl, phenyl, $C_1$-$C_6$ alkoxy, $C_1$-$C_6$ alkylthio, $C_1$-$C_6$ alkylsulfinyl, $C_7$-$C_9$ aralkoxy, phenoxy, phenylthio, phenylsulfonyl, alkali metal carboxylate $C_2$-$C_5$ alkoxycarbonyl or $-NR^5R^6$;

$R^3$ and $R^4$ are the same or different and are $C_1$-$C_4$ alkylsulfonyl, nitro, $-OCX_nX_{3-n}$ or any of the meanings given for $R^1$ and $R^2$;

$R^5$ and $R^6$ are the same or different and are hydrogen or $C_1$-$C_2$ alkyl;

X is fluorine, chlorine, or bromine; and n is 1, 2, or 3.

In yet further accordance with the instant invention a miticidal composition comprising the compound employed in the process for controlling mites, discussed immediately above, provided with a carrier therefor is set forth.

In still yet further accordance with the present invention a process for controlling nematodes is taught. In this process a nematocidally effective amount of at least one of the following compounds is applied to the locus to be protected: 2-(2-chlorophenyl)-4-phenyl-4H-1,3,4-oxadiazin-5(6H)-one (Compound No. 5); 2-(4-iodophenyl)-4-phenyl-4H-1,3,4-oxadiazin-5(6H)-one (Compound No. 11); 2-(2-methylphenyl)-4-phenyl-4H-1,3,4-oxadiazin-5(6H)-one (Compound No. 12); 2-(3-methylphenyl)-4-phenyl-4H-1,3,4-oxadiazin-5(6H)-one (Compound No. 13); 2-(4-methylphenyl)-4-phenyl-4H-1,3,4-oxadiazin-5(6H)-one (Compound No. 14); 2-(4-methoxyphenyl)-4-phenyl-4H-1,3,4-oxadiazin-5(6H)-one (Compound No. 29); 2-(2-ethoxyphenyl)-4-phenyl-4H-1,3,4-oxadiazin-5(6H)-one (Compound No. 30); 2-[3-(pentyloxy)phenyl]-4-phenyl-4H-1,3,4-oxadiazin-5(6H)-one (Compound No. 33); 2-(3-fluoro-4-methylphenyl)-4-phenyl-4H-1,3,4-oxadiazin-5(6H)-one (Compound No. 42); 2-(3-methyl-4-methoxyphenyl)-4-phenyl-4H-1,3,4-oxadiazin-5(6H)-one (Compound No. 47); 4-(4-methylphenyl)-2-phenyl-4H-1,3,4-oxadiazin-5(6H)-one (Compound No. 48); 2-(4-fluorophenyl-4-(4-methylphenyl)-4H-1,3,4-oxadiazin-5(6H)-one (Compound No. 49); 2-(4-chlorophenyl)-4-(4-methylphenyl)-4H-1,3,4-oxadiazin-5(6H)-one (Compound No. 50); 2-(4-butoxyphenyl)-4-(4-methylphenyl)-4H-1,3,4-oxadiazin-5(6H)-one (Compound No. 53); 2-(3,4-dimethylphenyl)-4-(4-methylphenyl)-4e,uns/H/ -1,3,4-oxadiazin-5(6H)-one (Compound No. 58); 2-(4-methylphenyl)-4-(3-methylphenyl)-4H-1,3,4-oxadiazin-5(6H)-one (Compound No. 59); 4-(2-bromophenyl)-2-(4-methylphenyl)-4H-1,3,4-oxadiazin-5(6H)-one (Compound No. 64); 4-(2-fluorophenyl)-2-(4-methylphenyl)-4-H-1,3,4-oxadiazin)-one (Compound No. 65); 4-(3-fluorophenyl)-2-(4-methylphenyl)-4H-1,3,4-oxadiazin-5(6H)-one (Compound No. 66); 4-(3-chloro-4-methylphenyl)-2-(4-methylphenyl)-4H-1,3,4-oxadiazin-6(6H)-one (Compound No. 72); 2-[4-(diethylamino)phenyl]-4-phenyl-4H-1,3,4-oxadiazin-5(6H)-one (Compound No. 79); 2-(4-aminophenyl)-4-phenyl-4H-1,3,4-oxadiazin-5(6H)-one (Compound No. 81), 2-(4-methylphenyl)-4-(4-nitrophenyl)-4H-1,3,4-oxadiazin-5(6H)-one (Compound No. 82); 4-(3-chloro-4-methylphenyl)-2-(3,4-dimethylphenyl)-4H-1,3,4-oxadiazin-5(6H)-one (Compound No. 84); and 2,4-bis(4-bromophenyl)-4H-1,3,4-oxadiazin-5(6H)-one (Compound No. 95).

It is noted that the structural formula of each of the above nematocidally effective compounds is provided. These structural formulae are defined in Table I supra in which the structure of each compound is defined by the compound number.

Another aspect of the present invention involves nematocidal compositions which each comprise the compounds, provided in the process for controlling nematodes, set forth immediately above, and a carrier therefor.

DETAILED DESCRIPTION

The present invention is directed to a class of substituted oxadiazinones represented by the structural formula

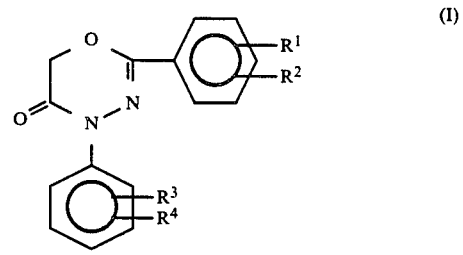

(I)

where $R^1$ and $R^2$ are the same or different and are hydrogen; however, $R^1$ and $R^2$ cannot both be hydrogen if $R^3$ and $R^4$ are both hydrogen or if one of $R^3$ and $R^4$ are hydrogen and the other nitro; in addition $R^1$ and $R^2$ may be the same or different and may be fluorine, chlorine, bromine, $C_1$-$C_6$ alkyl, $C_1$-$C_2$ haloalkyl, $C_3$-$C_6$ cycloalkyl, $C_7$-$C_9$ aralkyl, phenyl, $C_1$-$C_6$ alkoxy, $C_1$-$C_6$ alkylthio, $C_1$-$C_6$ alkylsulfinyl, $C_7$-$C_9$ aralkoxy, phenoxy, provided that if both $R^3$ and $R^4$ are hydrogen then $R^1$ and $R^2$ cannot be 3-phenoxy and hydrogen; also $R^1$ and $R^2$ may be the same or different and may be phenylthio, phenylsulfonyl, alkali metal carboxylate, $C_2$-$C_5$ alkoxycarbonyl, phenoxycarbonyl or $-NR^5R^6$;

$R^3$ and $R^4$ are the same or different and are $C_1$-$C_4$ alkylsulfonyl, nitro, provided that if the other of $R^3$ and $R^4$ is hydrogen then both $R^1$ and $R^2$ cannot be hydrogen; also $R^3$ and $R^4$ may be the same or different and may be $-OCX_nH_{3-n}$ or one of the meanings given for $R^1$ and $R^2$ with the proviso that if $R^3$ and $R^4$ are together hydrogen and bromine when $R^1$ and $R^2$ are both hydrogen then the bromine cannot be 4-bromo;

$R^5$ and $R^6$ are the same or different and are hydrogen or $C_1-C_2$ alkyl with the proviso that when $R^5$ and $R^6$ are both hydrogen then $R^1$, $R^2$ and $R^3$ cannot all by hydrogen;

X is fluorine, chlorine, or bromine; and n is 1, 2 or 3.

More preferably, the present invention is directed to a class of substituted oxadiazinones having the structural formula (I), where $R^1$ is hydrogen, fluorine, chlorine, 4-iodo, 2-trifluoromethyl, linear $C_1-C_4$ alkyl, 4-benzyl, $C_1-C_5$ alkoxy, $C_1-C_4$ alkylthio or 4-$NR^5R^6$;

$R^2$ is hydrogen, 4-chloro, $C_1-C_4$ alkyl or $C_1-C_4$ alkoxy;

$R^3$ and $R^4$ are the same or different and are hydrogen; with the proviso both $R^3$ and $R^4$ cannot both be hydrogen if $R^1$ and $R^2$ are hydrogen; $R^3$ and $R^4$ may also be the same or different and may be fluorine, chlorine, bromine, again with the proviso that if $R^3$ and $R^4$ are together hydrogen and bromine and both $R^1$ and $R^2$ are hydrogen then the bromine cannot be 4-bromo; $R^3$ and $R^4$ may also be the same or different and may be $C_1-C_4$ alkyl, benzyl, phenyl or $C_1-C_4$ alkoxy; and $R^5$ and $R^6$ are the same and are hydrogen or $C_1-C_2$ alkyl.

Still more preferably, the present invention is directed to a class of substituted oxadiazinones having the structural formula (I) where $R^1$ is hydrogen, fluorine, chlorine, linear $C_1-C_4$ alkyl in the 3- or 4-position, 4-benzyl, $C_1-C_4$ alkoxy in the 3- or 4-position or $C_1-C_4$ alkylthio in the 3- or 4-position;

$R^2$ is hydrogen, 4-chloro, 4-methyl, 5-methyl or 4-methoxy; and $R^3$ and $R^4$ are the same or different and are hydrogen, fluorine, chlorine, bromine, $C_1-C_2$ alkyl, benzyl, phenyl or methoxy with the same provisos regarding the cases where $R^3$ and $R^4$ are both hydrogen or hydrogen and bromine.

Another aspect of the present invention involves a process for forming the compounds having the structural formula (I) where the radicals have the definitions recited above for the broadest, preferred and more preferred embodiments. In the first step of this process a compound having the formula $R^1R^2C_6H_3COCl$ is reacted with a compound having the formula $R^3R^4C_6H_3NHNH_2$ where the radicals, $R^1$, $R^2$, $R^3$, $R^4$, $R^5$, $R^6$, X and n have the meanings given for the broadest, preferred or more preferred embodiments of the compound of the present invention. This reaction is preferably conducted in pyridine at a temperature in the range of between 10° and 40° C. More preferably, this reaction occurs at the temperature in the range of between 20° and 30° C. The reaction, which occurs at atmospheric pressure, is conducted for a period of between 1 and 6 hours. Upon completion of this period the reaction mixture is poured into ice water.

The product of the above first step of the process for forming the substituted oxadiazinones of the present invention is a first intermediate compound having the structural formula $R^1R^2C_6H_3CONHNHC_6H_3R^3R^4$. The first intermediate compound is reacted with chloroacetyl chloride. This reaction usually occurs with the first intermediate compound dissolved in a suitable solvent. Among the solvents preferred for use in this application are acetone or methylethyl ketone. The chloroacetyl chloride is preferably slowly added to the solution at room temperature. Thereafter, the reaction mixture is refluxed for a period of 4 to 10 hours. At this point a second intermediate product, having the structural formula $R^1R^2C_6H_3CONHN(COCH_2Cl)C_6H_3R^3R^4$ is formed. The reaction product of the second step is thereafter cooled. Thereupon, potassium carbonate, usually in powdered form, is added in excess to the reaction product. The mixture is then again heated to reflux for another 4 to 10 hours, preferably at atmospheric pressure. The cyclized product of this reaction is the substituted oxadazinone having the structural formula (I) and defined by the radicals therein.

The product of this process is isolated by first filtering off the solid potassium carbonate powder. Next, the solvent is evaporated followed by washing the product with an alcohol, preferably ethanol and filtering and drying the product.

The present invention is additionally directed to a process for controlling mites which comprises applying a miticidally effective amount of the compound having the structural formula (I) wherein $R^1$ and $R^2$ are the same or different and are hydrogen, fluorine, chlorine, bromine, iodine, $C_1-C_2$ fluoroalkyl, $C_1-C_2$ chloroalkyl, $C_1-C_2$ bromoalkyl, $C_1-C_6$ alkyl, $C_3-C_6$ cycloalkyl, $C_7-C_9$ aralkyl, phenyl, $C_1-C_6$ alkoxy, $C_1-C_6$ alkylthio, $C_1-C_6$ alkylsulfinyl, $C_7-C_9$ aralkoxy, phenoxy, phenylthio, phenylsulfonyl, alkali metal carboxylate, $C_2-C_5$ alkoxycarbonyl or $NR^5R^6$;

$R^3$ and $R^4$ are the same or different and are $C_1-C_4$ alkylsulfonyl, nitro, $-OCX_nX_{3-n}$ or one of the groups within the contemplation of $R^1$ and $R^2$;

$R^5$ and $R^6$ are the same or different and are hydrogen or $C_1-C_2$ alkyl;

X is fluorine, chlorine or bromine; and n is 1, 2 or 3.

More preferably, the present invention is directed to a process for controlling mites by applying a miticidally effective amount of a compound having the structural formula (I) wherein $R^1$ is hydrogen, fluorine, chlorine, 4-iodo, 2-trifluoromethyl, linear $C_1-C_4$ alkyl, 4-benzyl, $C_1-C_5$ alkoxy, $C_1-C_4$ alkylthio, 4-$NR^5R^6$;

$R^2$ is hydrogen, 4-chloro, $C_1-C_4$ alkyl or $C_1-C_4$ alkoxy;

$R^3$ and $R^4$ are the same or different and are hydrogen, fluorine, chlorine, bromine, $C_1-C_4$ alkyl, benzyl, phenyl, or $C_1-C_4$ alkoxy; and $R^5$ and $R^6$ are the same and are hydrogen or $C_1-C_2$ alkyl.

Still more preferably, the process for controlling mites is accomplished by applying a miticidally effective amount of the compound having the structural formula (I) where $R^1$ is hydrogen, fluorine, chlorine, linear $C_1-C_4$ alkyl in the 3- or 4-position, 4-benzyl, $C_1-C_4$ alkoxy in the 3- or 4-position or $C_1-C_4$ alkylthio in the 3- or 4-position;

$R^2$ is hydrogen, 4-chloro, 4-methyl, 3-methyl or 4-methoxy; and $R^3$ and $R^4$ are the same or different and are hydrogen, fluorine, chlorine, bromine, $C_1-C_2$ alkyl, benzyl, phenyl or 4-methoxy.

In yet another aspect of the present invention a miticidal composition is provided which comprises a compound within the class of compounds employed to control mites, set forth above, in combination with a carrier therefor. More preferably, the present invention is directed to a miticidal composition which comprises a compound within the contemplation of the more preferred class of compounds employed to control mites and a carrier therefor. Still more preferably, a miticidal composition comprising a compound within the class of the most preferred compounds for controlling mites and a carrier therefor.

In still another aspect of the present invention a process is provided for controlling nematodes. In this process a nematocidally effective amount of a compound selected from the group consisting of 2-(2-chlorophenyl)-4-phenyl-4H-1,3,4-oxadiazin-5(6H)-one (Compound No. 5), 2-(4-iodophenyl)-4-phenyl-4H-1,3,4-oxadiazin-5(6H)-one (Compound No. 11); 2-(2-methylphenyl)-4-phenyl-4H-1,3,4-oxadiazin-5(6H)-one (Compound No. 12); 2-(3-methylphenyl)-4-phenyl-4H-1,3,4-oxadiazin-5(6H)-one (Compound No. 13); 2-(4-methylphenyl)-4-phenyl-4H-1,3,4-oxadiazin-5(6H)-one (Compound No. 14); 2-(4-methoxyphenyl)-4-phenyl-4H-1,3,4-oxadiazin-5(6H)-one (Compound No. 29); 2-(2-ethoxyphenyl)-4-phenyl-4H-1,3,4-oxadiazin-5(6H)-one (Compound No. 30); 2-[3-(pentyloxy)phenyl]-4-phenyl-4H-1,3,4-oxadiazin-5(6H)-one (Compound No. 33); 2-(3-fluoro-4-methylphenyl)-4-phenyl-4H-1,3,4-oxadiazin-5(6H)-one (Compound No. 42); 2-(3-methyl-4-methoxyphenyl)-4-phenyl-4H-1,3,4-oxadiazin-5(6H)-one (Compound No. 47); 4-(4-methylphenyl)-2-phenyl-4H-1,3,4-oxadiazin-5(6H)-one (Compound No. 48); 2-(4-fluorophenyl-4-(4-methylphenyl)-4H-1,3,4-oxadiazin-5(6H)-one (Compound No. 49); 2-(4-chlorophenyl)-4-(4-methylphenyl)-4H-1,3,4-oxadiazin-5(6H)-one (Compound No. 50); 2-(4-butoxyphenyl)-4-(4-methylphenyl)-4H-1,3,4-oxadiazin-5(6H)-one (Compound No. 53); 2-(3,4-dimethylphenyl)-4-(4-methylphenyl)-4H-1,3,4-oxadiazin-5(6H)-one (Compound No. 58); 2-(4-methylphenyl)-4-(3-methylphenyl)-4H-1,3,4-oxadiazin-5(6H)-one (Compound No. 59); 4-(2-bromophenyl)-2-(4-methylphenyl)-4H-1,3,4-oxadiazin-5(6H)-one (Compound No. 64); 4-(2-fluorophenyl)-2-(4-methylphenyl)-4H-1,3,4-oxadiazin)-one (Compound No. 65); 4-(3-fluorophenyl)-2-(4-methylphenyl)-4H-1,3,4-oxadiazin-5(6H)-one (Compound No. 66); 4-(3chloro-4-methylphenyl)-2-(4-methylphenyl)-4H-1,3,4-oxadiazin-6(6H)-one (Compound No. 72); 2-[4-(diethylamino)phenyl]-4-phenyl-4H-1,3,4-oxadiazin-5(6H)-one (Compound No. 79); 2-(4-aminophenyl)-4-phenyl-4H-1,3,4-oxadiazin-5(6H)-one Compound No. 81); 2-(4-methylphenyl)-4-(4-nitrophenyl)-4H-1,3,4-oxadiazin-5(6H)-one (Compound No. 82); 4-(3-chloro-4-methylphenyl)-2-(3,4-dimethylphenyl)-4H-1,3,4-oxadiazin-5(6H)-one (Compound No. 84); 2,4-bis(4-bromophenyl)-4H-1,3,4-oxadiazin-5(6H)-one (Compound No. 95); and mixtures thereof is applied to the locus to be protected. It is again emphasized that above-named compounds are structurally defined by their parenthesized compound number defined in Table I.

The last aspect of the present invention is directed to a nematocidal composition comprising at least one of the twenty-five compounds effective in the control of nematodes in combination with a carrier therefor.

Both the nemacidal and miticidal compositions of this invention employ compounds defined above in combination with a carrier. The carrier, within the contemplation of the composition of this invention, may be a finely divided or granular organic or inorganic material. Among the inert carriers within the contemplation of this invention are attapulgite clay, sand, vermiculite, corncobs, activated carbon and mineral silicates such as mica, talc, pyrophyllite and clays.

In another preferred embodiment of the composition of this invention the composition comprises a solution. That is, the active agent, a compound whose structural formula is (I), is dissolved in a suitable solvent which acts as the carrier. Among the solvents within the contemplation of this invention are acetone, methanol, isopropanol, t-butyl alcohol, cyclohexanol, n-butyl alcohol, cyclohexanone, toluene, xylene, dioxane, dimethylformamide, dimethysulfoxide, ethylene dichloride and N-methylpyrrolidone.

In still another preferred embodiment of the composition within the contemplation of this invention, the composition comprises a water emulsion carrier. The emulsion is prepared from a solution as described immediately above. To the solution is added a surface active agent. Surface active agents suitable for use in forming the emulsion of this invention are known to those skilled in the art. McCutcheon's Detergents and Emulsifiers, Allured Publishing Corp., Ridgewood, N.J. (1970); U.S. Pat. No. 2,514,916, columns 2–4; and U.S. Pat. No. 2,547,734, columns 3 and 4 provide detailed examples of such surface active agents. These agents may be anionic, non-ionic or cationic.

In yet still another preferred embodiment of the composition of this invention, the composition employs a dispersant as carrier. In this embodiment, the active nematicidal or miticidal agent, the compound whose structural formula is (I), is mixed with a surface active agent of the type described above. Water is then added to form a dispersion. The amount of water added determines the concentration of the composition. The active agent may be added neat, that is, as a pure compound or may be premixed with a solvent of the type described above to form a solution which is added to the surface active agent and water.

In still another embodiment of the active compound is premixed with an inert solid carrier which is added to a surface active agent and water to provide yet another form of dispersion within the contemplation of the composition of this invention.

The embodiment discussed immediately above, the disposal of the active agent on a solid inert carrier, which is dispersed to form a dispersion, may alternatively be employed in non-liquid form. That is, the composition of this invention may take the form of a dust, granules, a paste or a wettable powder. In these embodiments the active compound of this invention, the compound having the structural formula (I), is admixed with the inert carrier to form a solid composition. Thus, for example, in the embodiment wherein a powder is formed, the solid inert carrier is provided in powder form. In many such cases, the inert carrier is a mineral silicate. The solid may be made wettable by the addition of a surface active agent, well known to those skilled in the art, and referred to in the above-recited references directed to surface active agents.

In another principal application of the composition of this invention an aerosol in prepared. To prepare an aerosol the active compound is dissolved in a first solvent. This first solvent is conventional in the sense that although the first solvent is volatile it is not highly volatile. This solution is then admixed with a highly volatile solvent, a so-called liquid aerosol carrier. The aerosol carrier is liquid only under elevated pressure. At ordinary temperatures and at atmospheric pressure, the aerosol carrier is a gas. In a subembodiment of this preferred embodiment, the aerosol carrier may itself be active. For example, the carrier may be insecticide, a herbicide, a bacteriacide or a plant growth regulant.

The following examples are given to illustrate the scope of the present invention. Because these examples are given for illustrative purposes only, the invention embodied therein should not be limited to the actual examples provided.

EXAMPLE 1

Preparation of 2,4-Bis(4-methylphenyl)-4H-1,3,4-oxadiazin-5(6H)-one (Compound No. 55)

To a stirred solution of 15.8 grams of p-tolyl hydrazine hydrochloride, in 200 ml. of pyridine, was added, dropwise, 15.4 g. of p-toluoyl chloride at room temperature. After this addition, the mixture was stirred at room temperature for three hours. The mixture was then poured into 700 ml of ice water. After standing overnight a solid was observed which was filtered and washed with water. Twenty-two grams of 2-(4-methyphenyl)hydrazide of 4-methylbenzoic acid was thus obtained.

Four ml. of chloroacetyl chloride was added dropwise to a stirred solution of 12 g. of the product of the above reaction, 2-(4-methyphenyl)hydrazide of 4-methylbenzoic acid, in 200 ml. of methylethyl ketone. After this addition, which occurred at room temperature, the mixture was refluxed for four hours, cooled to room temperature and treated with 19 g. of potassium carbonate powder. The mixture was then refluxed, again for four hours. The product was filtered while hot and the solvent then evaporated under reduced pressure. The resulting solid was washed with ethanol and filtered. The final product obtained was 6 gms. of 2,4-bis(4-methylphenyl)-4H-1,3,4-oxadiazin-5-(6H)-one.

The product obtained was tested to determine its melting point at atmospheric pressure. The melting point of this compound was 100°–102° C.

EXAMPLE 2

Preparation of Compounds 1–54 and 56–82

Additional compounds were prepared using essentially the process of Example 1. Where starting compounds were not commercially available they were synthesized by methods well known in the art. These compounds, including Compound No. 55 whose preparation is described in Example 1, are summarized in Table I below. Each of the compounds so formed are characterized by its melting point and/or their NMR characteristics. Table I includes melting temperature data. Certain of these compounds which are oils at ambient condition or for which a melting point was not obtained are defined by NMR characteristics. A tabulation of the NMR data is provided in Table II.

TABLE I

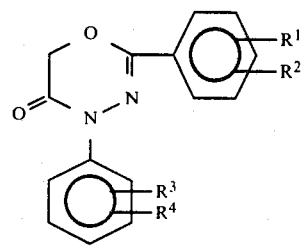

| Cpd. No. | $R^1$ | $R^2$ | $R^3$ | $R^4$ | m.p., °C. |
|---|---|---|---|---|---|
| 1 | H | H | H | H | 95–8 |
| 2 | 2-F | H | H | H | 70–3 |
| 3 | 3-F | H | H | H | Oil |
| 4 | 4-F | H | H | H | 100–2 |
| 5 | 2-Cl | H | H | H | 93–5 |
| 6 | 3-Cl | H | H | H | 112–4 |
| 7 | 4-Cl | H | H | H | 124–6 |
| 8 | 2-Br | H | H | H | 115–7 |
| 9 | 2-I | H | H | H | 107–8 |
| 10 | 3-I | H | H | H | 115–8 |
| 11 | 4-I | H | H | H | 129–32 |
| 12 | 2-$CH_3$ | H | H | H | 72–4 |
| 13 | 3-$CH_3$ | H | H | H | 92–4 |
| 14 | 4-$CH_3$ | H | H | H | 62–64 |
| 15 | 4-$C_2H_5$ | H | H | H | 97–8 |
| 16 | 4-$nC_4H_9$ | H | H | H | Oil |
| 17 | 4-$tC_4H_9$ | H | H | H | 102–4 |
| 18 | 2-$CH_2C_6H_5$ | H | H | H | 92–4 |
| 19 | 3-$CH_2C_6H_5$ | H | H | H | Oil |
| 20 | 4-$CH_2C_6H_5$ | H | H | H | 82–3 |
| 21 | 2-$CF_3$ | H | H | H | 81–2 |
| 22 | 3-$CF_3$ | H | H | H | 91–93 |
| 23 | 4-$CF_3$ | H | H | H | 115–7 |
| 24 | 2-$COOC_3H_7$ | H | H | H | Oil |
| 25 | 2-$COOC_6H_5$ | H | H | H | 124–5 |
| 26 | 2-COONa | H | H | H | 300+ |
| 27 | 2-$OCH_3$ | H | H | H | 91–93 |
| 28 | 3-$OCH_3$ | H | H | H | 98–100 |
| 29 | 4-$OCH_3$ | H | H | H | NA |
| 30 | 2-$OC_2H_5$ | H | H | H | 83–5 |
| 31 | 4-$OC_2H_5$ | H | H | H | 145–7 |
| 32 | 4-$OC_4H_9$ | H | H | H | 90–3 |
| 33 | 3-$OC_5H_{11}$ | H | H | H | oil |
| 34 | 2-$OCH_2C_6H_5$ | H | H | H | 85–7 |
| 35 | 4-$SCH_3$ | H | H | H | oil |
| 36 | 4-$SC_2H_5$ | H | H | H | 82–5 |
| 37 | 3-$SC_6H_5$ | H | H | H | 85–7 |
| 38 | 4-$SOCH_3$ | H | H | H | 95–7 |
| 39 | 3-Cl | 4-Cl | H | H | 90–2 |
| 40 | 2-Cl | 6-Cl | H | H | 86–8 |
| 41 | 3-Cl | 5-Cl | H | H | 143–5 |
| 42 | 3-F | 4-$CH_3$ | H | H | 82–4 |
| 43 | 3-$CH_3$ | 4-$CH_3$ | H | H | 88–90 |
| 44 | 3-$CH_3$ | 5-$CH_3$ | H | H | 115–6 |
| 45 | 3-$OCH_3$ | 4-$OCH_3$ | H | H | 153–5 |
| 46 | 3-$OCH_3$ | 5-$OCH_3$ | H | H | 109–11 |
| 47 | 3-$CH_3$ | 4-$OCH_3$ | H | H | 104–7 |
| 48 | H | H | 4-$CH_3$ | H | 102–4 |
| 49 | 4-F | H | 4-$CH_3$ | H | 142–4 |
| 50 | 4-Cl | H | 4-$CH_3$ | H | 120–2 |
| 51 | 4-I | H | 4-$CH_3$ | H | 150–1 |
| 52 | 4-$OCH_3$ | H | 4-$CH_3$ | H | 97–9 |
| 53 | 4-$OC_4H_9$ | H | 4-$CH_3$ | H | 105–7 |
| 54 | 4-$SC_2H_5$ | H | 4-$CH_3$ | H | 93–5 |
| 55 | 4-$CH_3$ | H | 4-$CH_3$ | H | 100–2 |
| 56 | 4-$C_2H_5$ | H | 4-$CH_3$ | H | 70–2 |
| 57 | 3-Cl | 4-Cl | 4-$CH_3$ | H | 160–1 |
| 58 | 3-$CH_3$ | 4-$CH_3$ | 4-$CH_3$ | H | 94–5 |
| 59 | 4-$CH_3$ | H | 3-$CH_3$ | H | 80–2 |
| 60 | 4-$CH_3$ | H | 2-$CH_2C_6H_5$ | H | 125–7 |
| 61 | 4-$CH_3$ | H | 3-$CH_3$ | 4-$CH_3$ | 102–6 |
| 62 | 4-$CH_3$ | H | 3-$OCH_3$ | H | 105–7 |
| 63 | 4-$CH_3$ | H | 4-$OCH_3$ | H | 119–21 |
| 64 | 4-$CH_3$ | H | 2-Br | H | 128–30 |
| 65 | 4-$CH_3$ | H | 2-F | H | 137–9 |
| 66 | 4-$CH_3$ | H | 3-F | H | 102–4 |
| 67 | 4-$CH_3$ | H | 4-Br | H | 117–9 |

TABLE I-continued

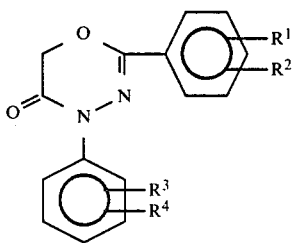

| Cpd. No. | R¹ | R² | R³ | R⁴ | m.p., °C. |
|---|---|---|---|---|---|
| 68 | 4-$CH_3$ | H | 4-F | H | 93-5 |
| 69 | 4-$CH_3$ | H | 2-Cl | 5-Cl | 150-2 |
| 70 | 4-$CH_3$ | H | 2-Cl | 6-Cl | 134-5 |
| 71 | 4-$CH_3$ | H | 3-Cl | 4-Cl | 142-4 |
| 72 | 4-$CH_3$ | H | 3-Cl | 4-$CH_3$ | 144-5 |
| 73 | 4-$CH_3$ | H | 2-$SO_2C_6H_5$ | H | NA |
| 74 | 4-$CH_3$ | H | 2-$C_6H_5$ | H | 130-1 |
| 75 | 4-$CH_3$ | H | 4-$SO_2CH_3$ | H | 163-6 |
| 76 | 4-$CH_3$ | H | 4-$C_2H_5$ | H | 76-7 |
| 77 | 4-$N(CH_3)_2$ | H | H | H | 154-6 |
| 78 | 3-$N(C_2H_5)_2$ | H | H | H | oil |
| 79 | 4-$N(C_2H_5)_2$ | H | H | H | 92-5 |
| 80 | 4-$CH_3$ | H | $cC_6H_{11}$ | H | 107-8 |
| 81 | 4-$NH_2$ | H | H | H | 134-5 |
| 82 | 4-$CH_3$ | H | 4-$NO_2$ | H | NA |
| 83 | 3-Cl | 4-Cl | 4-$OCH_3$ | H | 138-40 |
| 84 | 3-$CH_3$ | 4-$CH_3$ | 3-Cl | 4-$CH_3$ | 85-6 |
| 85 | 4-$CH_3$ | H | 4-$OCH_2C_6H_5$ | H | 103-5 |
| 86 | 4-$OC_4H_9$ | H | 3-Cl | 4-$CH_3$ | 105-7 |
| 87 | 4-$CH_3$ | H | 3-$NH_2$ | H | 205-10 |
| 88 | 4-$CH_3$ | H | 3-$OCH_2C_6H_5$ | H | 82-4 |
| 89 | 4-$CH_3$ | H | 4-$NH_2$ | H | 158-60 |
| 90 | 3-$CH_3$ | H | 4-$OCH_3$ | H | 87-90 |
| 91 | 3-$CH_3$ | H | 3-$CH_3$ | H | 70-2 |
| 92 | 4-$OC_6H_5$ | H | 4-$CH_3$ | H | 126-9 |
| 93 | 3-$OCH_3$ | H | 3-Cl | 4-$CH_3$ | 96-8 |
| 94 | 3-$OCH_3$ | H | 4-$CH_3$ | H | NA |
| 95 | 4-Br | H | 4-Br | H | 157-9 |
| 96 | 4-$OCH_3$ | H | 4-$OCH_3$ | H | 85-7 |

REMARKS:
NA — Not Available

TABLE II
COMPOUNDS CHARACTERIZED BY NMR DATA

| Compound No. | NMR Characteristics |
|---|---|
| 3 | S(2) 4.8; m(9) 7.1-7.8 |
| 16 | t(3) 0.9; m(4) 1.4-1.8; t(2) 2.7; S(2) 4.8; m(9) 7.2-7. |
| 19 | S(2) 3.9; S(2) 4.7; m(14) 7.1-7. |
| 24 | t(3) 0.9; m(2) 1.6; t(2) 4.1; S(2) 4.9; m(9) 7.2-8.5 |
| 29 | S(3) 3.7; S(2) 4.7; m(9) 6.8-7.8 |
| 33 | t(3) 1.9; m(6) 1.1-1.8; t(3) 3.9; S(2) 4.7; m(9) 6.9-7.8 |
| 35 | S(3) 2.5; S(2) 4.8; m(9) 7.1-7.8 |
| 73 | S(3) 2.3; S(2) 4.8; m(13) 7.1-8.3 |
| 78 | t(6) 1.2; q(4) 3.3; S(2) 4.8; m(9) 6.7-7.7 |
| 82 | S(3) 2.4; S(2) 4.8; m(8) 7.1-8.3 |
| 94 | S(3) 2.3; S(3) 3.7; S(2) 4.8; m(8) 6.9-7.6 |

REMARKS:
(1) S = singlet, d = doublet, t = triplet, q = quartet and m = multiplet
(2) The number in parenthesis represents the number of protons.

EXAMPLE 3
Compounds 83-90

Additional compounds, within the contemplation of the present invention, are synthesized in accordance with the procedure of Example 1. These additional compounds are tabulated below in Table III. It is emphasized that meanings of R¹, R², R³ and R⁴ refer to radicals in the structural formula defined in Table I.

TABLE III

| Cpd. No. | R¹ | R² | R³ | R⁴ |
|---|---|---|---|---|
| 97 | $CH_2Cl$ | H | $OC_6H_{13}$ | H |
| 98 | $C_6H_{13}$ | H | $SC_6H_{13}$ | H |
| 99 | $CH_2CH_2Cl$ | H | $COOCH_3$ | H |
| 100 | $cC_3H_5$ | H | $SO_2C_4H_9$ | H |
| 101 | $(CH_2)_3C_6H_5$ | H | $O(CH_2)_3C_6H_5$ | H |
| 102 | $SOC_6H_{13}$ | H | $cC_6H_{11}$ | H |
| 103 | $OC_6H_5$ | H | $OCF_3$ | H |
| 104 | $C_6H_5$ | H | $OCHCl_2$ | H |

EXAMPLE 4
Control of Mites

Dispersions of Compound Nos. 1–80 and 83–96, defined in Table I, were prepared such that the test compounds were present in a concentration of 1,000 parts per million (ppm).[1] Cowpeas, in the first primary leaf stage, were used in the test. Two plants per pot, one primary leaf each, were used for each replicate. Two replicates were used for each compound tested. The plants were sprayed with the dispersions using a spray atomizer to thoroughly drench the foliage.

[1]Test dispersions in all examples are made by dissolving 300 mg of the active ingredient in 10 ml of acetone to which 30 mg of an emulsifying agent, ethoxylated sorbitan monolaurate, is added. Dilution with distilled water achieves the final concentrations.

One day following treatment, a circle of tree tanglefoot was placed on the upper surface of the treated leaves and adult mites, *Tetranychus urticae* Koch, were transferred into this confinement.

Six days following infestation with the mites, the plants were examined for adult live mites remaining on the leaves. On an estimated basis, in comparison with the number of living mites on the control plants, the percent control was determined. The results of this test are summarized in Table IV which appears below.

TABLE IV

| Compound No. | Miticidal Control, % |
|---|---|
| 1 | 100 |
| 2 | 90 |
| 3 | 65 |
| 4 | 100 |
| 5 | 30* |
| 6 | 92 |
| 7 | 100 |
| 8 | 34 |
| 9 | 17 |
| 10 | 32 |
| 11 | 100 |
| 12 | 70 |
| 13 | 100 |
| 14 | 100 |
| 15 | 93 |
| 16 | 100 |
| 17 | 60 |
| 18 | 22 |
| 19 | 22 |
| 20 | 96 |
| 21 | 81 |
| 22 | 55 |
| 23 | 64 |
| 24 | 5 |
| 25 | 20* |
| 26 | 37** |
| 27 | 25 |
| 28 | 100 |
| 29 | 100 |
| 30 | 93 |
| 31 | 30 |
| 32 | 93 |

TABLE IV-continued

| Compound No. | Miticidal Control, % |
| --- | --- |
| 33 | 100 |
| 34 | 25* |
| 35 | 39* |
| 36 | 95 |
| 37 | 50 |
| 38 | 34 |
| 39 | 100 |
| 40 | 20 |
| 41 | 46 |
| 42 | 90 |
| 43 | 100 |
| 44 | 90 |
| 45 | 34 |
| 46 | 59 |
| 47 | 90 |
| 48 | 90 |
| 49 | 90 |
| 50 | 100 |
| 51 | 70 |
| 52 | 95 |
| 53 | 60 |
| 54 | 100 |
| 55 | 100 |
| 56 | 100 |
| 57 | 80 |
| 58 | 95 |
| 59 | 100 |
| 60 | 95 |
| 61 | 80 |
| 62 | 95 |
| 63 | 100 |
| 64 | 23*** |
| 65 | 43*** |
| 66 | 50 |
| 67 | 100 |
| 68 | 95 |
| 69 | 90 |
| 70 | 70 |
| 71 | 95 |
| 72 | 90 |
| 73 | 33*** |
| 74 | 100 |
| 75 | 70 |
| 76 | 95 |
| 77 | 37 |
| 78 | 32 |
| 79 | 80 |
| 80 | 50 |
| 83 | 85 |
| 84 | 85 |
| 85 | 80 |
| 86 | 0 |
| 87 | 0 |
| 88 | 90 |
| 89 | 20 |
| 90 | 100 |
| 91 | 90 |
| 92 | 60 |
| 93 | 95 |
| 94 | 95 |
| 95 | 96 |
| 96 | 74 |

Remarks:
*Tested at 2,000 ppm
**Tested at 5,000 ppm
***Tested at 500 ppm

EXAMPLE 5

Nematode Soil Test

The Southern root-knot nematode, *Meloidogyne incognita*, was reared in sandy culture soil using tomato as host plant. Roots from culture plants were ground in a Waring [trademark] blender. Ground roots and culture soil were mixed with equal parts of uninfested soil. This mixture was placed in pots.

Dispersions were prepared using twenty-three compounds defined in Table I at a concentration of 1,000 ppm. Each of these dispersions were added to the above-described pots drenching each pot with 25 ml of the dispersion which was further diluted to provide a resultant soil concentration of 50 ppm.

One day after treatment with the 50 ppm dispersions, two tomato seedlings were planted in each pot. Twelve days after planting, the roots were evaluated by washing away the soil and comparing the number of knots on plant roots from the treated soil with the number of knots noted on untreated nematode-infested controls. These controls were prepared and grown identically with the treated pots. However, these pots were not treated with a dispersion of any of the compounds within the contemplation of this invention.

The results of this nematode soil test are summarized below in Table V.

TABLE V

Nematocidal Activity (at 50 ppm)

| Cpd. No. | % Control |
| --- | --- |
| 5 | 50 |
| 11 | 60 |
| 12 | 75 |
| 13 | 75 |
| 14 | 50 |
| 29 | 75 |
| 30 | 95 |
| 33 | 50 |
| 42 | 70 |
| 47 | 60 |
| 48 | 65 |
| 49 | 80 |
| 50 | 50 |
| 53 | 80 |
| 58 | 50 |
| 59 | 50 |
| 64 | 70 |
| 65 | 80 |
| 66 | 50 |
| 72 | 50 |
| 79 | 50 |
| 81 | 85 |
| 82 | 80 |
| 84 | 60 |
| 95 | 60 |

The above embodiments and examples illustrate the scope and spirit of the instant invention. These embodiments and examples will make apparent, to those skilled in the art, other embodiments and examples. These other embodiments and examples are within the contemplation of this invention. Therefore, the instant invention should be limited only by the appended claims.

What is claimed is:

1. A compound having the structural formula

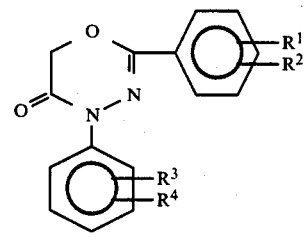

where $R^1$ and $R^2$ are the same or different and are hydrogen; however, both $R^1$ and $R^2$ cannot both be hydrogen if $R^3$ and $R^4$ are both hydrogen; in addition $R^1$ and $R^2$ are the same or different and are fluorine, chlorine, [bromine,] iodine, $C_1$–$C_6$ alkyl, $C_1$–$C_2$ haloalkyl, $C_3$–$C_6$ cycloalkyl, $C_7$–$C_9$ aralkyl, phenyl, $C_1$–$C_6$ alkoxy, $C_1$–$C_6$ alkylthio, $C_1$–$C_6$ alkylsulfinyl, $C_7$–$C_9$ aralkoxy, phenoxy, provided that if both $R^3$ and $R^4$ are hydrogen, then $R^1$ and $R^2$ cannot be 3-phenoxy and hydrogen; also $R^1$ and $R^2$ are the same or different and are phenylthio, phenylsulfinyl, alkali metal carboxylate, $C_2$–$C_5$ alkoxycarbonyl, phenoxycarbonyl or —$NR^5R^6$;

$R^3$ and $R^4$ are the same or different and are $C_1$–$C_4$ alkylsulfonyl, nitro; provided that if the other of $R^3$ and $R^4$ is hydrogen then both $R^1$ and $R^2$ cannot be hydrogen; also $R^3$ and $R^4$ are the same or different and are —$OCX_nH_{3-n}$ or are fluorine, chlorine, bromine, iodine, $C_1$–$C_6$ alkyl, $C_1$–$C_2$ haloalkyl, $C_3$–$C_6$ cycloalkyl, $C_7$–$C_9$ aralkyl, phenyl, $C_1$–$C_6$ alkoxy, $C_1$–$C_6$ alkylthio, $C_1$–$C_6$ alkysulfinyl, $C_7$–$C_9$ aralkoxy, phenoxy, phenylthio, phenylsulfinyl, alkali metal carboxylate, $C_2$–$C_5$ alkoxycarbonyl, phenoxycarbonyl or —$NR^5R^6$; with the proviso that if $R^3$ and $R^4$ are together hydrogen and bromine than if $R^1$ and $R^2$ are both hydrogen the bromine cannot be 4-bromo;

$R^5$ and $R^6$ are the same or different and are hydrogen or $C_1$–$C_2$ alkyl with the proviso that when $R^5$ and $R^6$ are both hydrogen then $R^1$, $R^2$ and $R^3$ cannot all by hydrogen;

X is fluorine, chlorine or bromine; and n is 1, 2 or 3.

2. A compound in accordance with claim 1 wherein $R^1$ is hydrogen, fluorine, chlorine, 4-iodo, 2-trifluoromethyl, linear $C_1$–$C_4$ alkyl, 4-benzyl, $C_1$–$C_5$ alkoxy, $C_1$–$C_4$ alkylthio or 4-$NR^5R^6$;

$R^2$ is hydrogen, 4-chloro, $C_1$–$C_4$ alkyl or $C_1$–$C_4$ alkoxy;

$R^3$ and $R^4$ are the same or different and are hydrogen; with the proviso that both $R^3$ and $R^4$ cannot both be hydrogen if $R^1$ and $R^2$ are both hydrogen; also $R^3$ and $R^4$ are the same or different and are fluorine, chlorine and bromine; with the proviso that if $R^3$ and $R^4$ are together hydrogen and bromine and both $R^1$ and $R^2$ are hydrogen then the bromine cannot be 4-bromo; also $R^3$ and $R^4$ are the same or different and are $C_1$–$C_4$ alkyl, benzyl, phenyl or $C_1$–$C_4$ alkoxy; and $R^5$ and $R^6$ are the same or different and are hydrogen, or $C_1$–$C_2$ alkyl with the proviso that when $R^5$ and $R^6$ are both hydrogen then $R^1$, $R^2$ and $R^3$ cannot all be hydrogen.

3. A compound in accordance with claim 2 wherein $R^1$ is hydrogen, fluorine, chlorine, linear $C_1$–$C_4$ alkyl in the 3- or 4-position, 4-benzyl, $C_1$–$C_4$ alkoxy in the 3- or 4-position or $C_1$–$C_4$ alkylthio in the 3- or 4-position;

$R^2$ is hydrogen, 4-chloro, 4-methyl, 3-methyl or 4-methoxy; and $R^3$ and $R^4$ are the same or different and are hydrogen; with the proviso that both $R^3$ and $R^4$ cannot both be hydrogen if $R^1$ and $R^2$ are hydrogen; also $R^3$ and $R^4$ are the same or different and are bromine with the proviso that if $R^3$ and $R^4$ are together hydrogen and bromine and both $R^1$ and $R^2$ are hydrogen than bromine cannot be 4-bromo; also $R^3$ and $R^4$ are the same or different and are fluorine, chlorine, $C_1$–$C_2$ alkyl, benzyl, phenyl or methoxy.

* * * * *

UNITED STATES PATENT AND TRADEMARK OFFICE
CERTIFICATE OF CORRECTION

PATENT NO. : 4,670,555
DATED : 06/02/87
INVENTOR(S) : Mark A. Dekeyser, Anupama Mishra and Richard C. Moore It is certified that error appears in the above-identified patent and that said Letters Patent is hereby corrected as shown below:

At column 15, line 25 delete the phrase "$R^1$, $R^2$ and $R^3$" and substitute therefor the phrase -- $R^2$, $R^3$ and $R^4$ --.

Signed and Sealed this

Third Day of January, 1989

Attest:

DONALD J. QUIGG

*Attesting Officer*   *Commissioner of Patents and Trademarks*